US010933080B2

(12) United States Patent
Yoon et al.

(10) Patent No.: US 10,933,080 B2
(45) Date of Patent: Mar. 2, 2021

(54) MATERIALS FOR PREVENTING OR TREATING ALZHEIMER'S DISEASE AND COMPOSITIONS COMPRISING SAME

(71) Applicant: Research & Business Foundation Sungkyunkwan University, Suwon-si (KR)

(72) Inventors: Keejung Yoon, Gwacheon-si (KR); Juwan Kim, Suwon-si (KR)

(73) Assignee: Research & Business Foundation Sungkyunkwan University, Suwon-si (KR)

(*) Notice: Subject to any disclaimer, the term of this patent is extended or adjusted under 35 U.S.C. 154(b) by 0 days.

(21) Appl. No.: 16/454,202

(22) Filed: Jun. 27, 2019

(65) Prior Publication Data

US 2020/0000838 A1 Jan. 2, 2020

(30) Foreign Application Priority Data

Jun. 28, 2018 (KR) ........................ 10-2018-0074605

(51) Int. Cl.
*A61K 31/7105* (2006.01)
*G01N 33/68* (2006.01)

(52) U.S. Cl.
CPC ..... *A61K 31/7105* (2013.01); *G01N 33/6896* (2013.01); *G01N 2800/2821* (2013.01); *G01N 2800/52* (2013.01)

(58) Field of Classification Search
None
See application file for complete search history.

(56) References Cited

U.S. PATENT DOCUMENTS

2014/0304845 A1   10/2014   Loboda et al.

FOREIGN PATENT DOCUMENTS

| JP | 2012-135304 A | 7/2012 | |
| KR | 10-2014-0007979 A | 1/2014 | |
| WO | WO-2017020982 A1 * | 2/2017 | ........... A61K 31/713 |

OTHER PUBLICATIONS

Wiernasz et al. Neurochem Res 39: 2516-2526 (Year: 2014).*
Folch et al. Neurologia 33:47-58 (Year: 2018).*
Juwan Kim, "The Role of Ttyh1 in Notch Signaling Pathway during Mammalian Corticogenesis", Master's Thesis the Graduate School Sungkyunkwan University Department of Biotechnology and Bioengineering, Dec. 31, 2017, pp. 1-139.
Barbara Tate et al., "Modulation of Gamma-Secretase for the Treatment of Alzheimer's Disease", 2012, vol. 2012, Article ID 210756, pp. 1-11.
Mus pahari "PREDICTED: Mus pahari tweety family member 1 (Ttyh1), transcript variant X1, mRNA", 2019 (2 pages in English).

* cited by examiner

Primary Examiner — Brian Whiteman
(74) Attorney, Agent, or Firm — NSIP Law (57) ABSTRACT

The present invention relates to a composition comprising a Ttyh1 gene expression inhibitor or a Ttyh1 protein activity inhibitor, and a method of preventing or treating Alzheimer's disease using the same.

4 Claims, 8 Drawing Sheets

Specification includes a Sequence Listing.

MATERIALS FOR PREVENTING OR TREATING ALZHEIMER'S DISEASE AND COMPOSITIONS COMPRISING SAME

GOVERNMENT INTEREST

The claimed invention was undertaken with the support of "Study of effects of TRBP on brain cancer stem cell" Grant No. 1711065602, funded by the Ministry of Science and ICT of Republic of Korea.

CROSS-REFERENCE TO RELATED APPLICATION

This application claims the benefit under 35 USC 119(a) of Korean Patent Application No. 10-2018-0074605 filed on Jun. 28, 2018, in the Korean Intellectual Property Office, the entire disclosure of which is incorporated herein by reference for all purposes.

BACKGROUND

1. Field of the Invention

The present invention relates to a composition for preventing or treating Alzheimer's disease, which comprises an RNAi molecule specifically binding to Ttyh1 gene as an active ingredient, and more particularly, to a material for regulating the expression of Ttyh1 associated with the activity of γ-secretase known to play a role in promoting amyloid β expression by cleaving and then translocating the intracellular domain of an amyloid precursor protein (APP) in order to reduce amyloid β production, which is one of the causes of Alzheimer's disease, and a method of regulating the expression using the material.

2. Discussion of Related Art

For brain development of a mammal, production of various types of nerve cells such as neurons, astrocytes, and oligodendrocytes and accurate regulation thereof are necessary. The differentiation of embryonic nerve cells that determine the type of neurons or glial cell is regulated by several signaling pathways such as Notch, Sonic hedgehog (Shh) and Wnt pathways and the microenvironments of cells. Due to these signaling pathways, a balance between the number of neural stem cells and the number of differentiated cells produced may be maintained. In the initial step of the brain development, neuroepithelial cells are divided symmetrically to amplify the pool of neural stem cells, as development progresses, a neurogenic cycle begins, and the neural stem cells produce differentiated nerve cells such as intermediate precursor cells or neural stem cells through asymmetric division.

Notch receptors are cell membrane proteins that determine cell destiny in numerous tissues and organs, and regulate critical events of cells such as cell proliferation, cell death, etc. There are four Notch receptors in vertebrates, these receptors have similar structures and share ligands, but play different functional roles due to differences in embryonic tissue and spatio-temporally different differentiation patterns in adults. The interaction between a Notch receptor and a ligand such as Delta-like 1 (Dll1), Dll3, Dll4, Jagged1 (Jag1) or Jag2 leads to the initiation of a signal transduction system by direct cell-to-cell contact enabling this. In ligand binding, the intracellular region of Notch is cleaved by the activity of γ-secretase close to a transmembrane domain such that the Notch intracellular domain (NICD) is released. And then, NICD is transferred to the nucleus and bound with Notch coactivators such as CBF1 and Mastermind-like 1 (MAML1) so as to activate the expression of a Notch target gene.

A *Drosophila melanogaster* tweety (Tty) gene was originally isolated as a transcription unit adjacent to a fightless 1 gene, three mammalian Tty homologs, such as Ttyh1, Ttyh2 and Ttyh3, were identified based on the homology of a base sequence with respect to a *Drosophila* Tty protein. A protein sequence analysis showed that the Ttyh group includes complete membrane proteins including five transmembrane regions and can serve as chlorine channels. In addition, from the previous research confirming that Ttyh2 is a gene upregulated in the kidney and colon cancer, it was possible to assume that Ttyh is a potent regulator of cell proliferation, and this hypothesis is supported by research confirming that Ttyh1 is important in growth of glioblastoma, and the downregulation of Ttyh1 reduces tumor progression. It was revealed that Ttyh1, which is more relevant to this research, is present in neural stem cells and highly expressed in the ventricular zone (VZ) where active cell proliferation occurs in the developing mammalian brain. Therefore, Ttyh1 has been used as a marker for embryonic apical neural precursor cells, but the exact role and mechanism of Ttyh1 in the brain have not been revealed.

In the present invention, it was shown that Ttyh1 stimulates a Notch signaling pathway to improve characteristics of embryonic neural stem cells, and it was revealed that endoplasmic reticulum 1 (Red), which is a down-regulator of γ-secretase activity, becomes a direct target of Ttyh1, and thus Ttyh1 affects the Notch signaling pathway, thereby providing a mechanism which could potentially affect brain development. Moreover, it was found that γ-secretase releases the intracellular domain of an amyloid precursor protein in a similar manner to that for a Notch receptor, and translocates it into the nucleus to bind with an amyloid β expression-associated factor. Accordingly, the inventors confirmed that γ-secretase and amyloid β can have a critical effect on dementia, and when the expression of the Ttyh1 gene having a function of regulating amyloid activity, which has been found from this research, was regulated, it is effective in treatment of Alzheimer's disease, and thus the present invention was completed.

PRIOR ART DOCUMENTS

Patent Document

Korean Patent Application No. 10-2013-7035150
Japanese Patent Application No. 2011-266664

SUMMARY OF THE INVENTION

The present invention is directed to providing a composition for preventing or treating Alzheimer's disease, which comprises a Ttyh1 gene expression inhibitor or a Ttyh1 protein activity inhibitor as an active ingredient, and serves as a material capable of reducing amyloid β accumulation by regulating the expression of Ttyh1 gene.

The present invention is also directed to providing a pharmaceutical composition for preventing or treating Alzheimer's disease or a health functional food for preventing or improving Alzheimer's disease, which comprises the composition described above.

The present invention is also directed to providing a method of screening a material for preventing or treating Alzheimer's disease by regulating the expression and activity of Ttyh1 protein.

To attain the above-mentioned objects, the present invention provides a composition for preventing or treating Alzheimer's disease, which comprises a Ttyh1 expression inhibitor or an activity inhibitor as an active ingredient. As a material capable of reducing amyloid β accumulation by regulating the expression of Ttyh1 gene, the present invention particularly provides a composition for preventing or treating Alzheimer's disease, which comprises an RNAi molecule specifically binding to the Ttyh1 gene as an active ingredient.

The term "Alzheimer's disease" used herein is a type of dementia, which is one of the degenerative brain diseases. Particularly, it has been identified that Alzheimer's disease is caused by the accumulation of the amyloid β protein, and it has been known that the induction of the degeneration and death of nerve cells caused by the amyloid protein is involved in the mechanism of Alzheimer's disease. In the present invention, according to a mechanism of expressing amyloid β by releasing the intracellular domain of an amyloid precursor protein (APP), which is a precursor of the amyloid β protein, by γ-secretase and translocating the released intracellular domain into the nucleus, the accumulation of amyloid β was reduced by the regulation of expression of *Drosophila melanogaster* tweety homolog 1 (Ttyh1), which is a material that increases the activity of γ-secretase, thereby having an effect of preventing, improving and treating Alzheimer's disease.

According to an exemplary embodiment of the present invention, the composition of the present invention comprises a material for regulating Ttyh1 gene expression or a material for directly inhibiting Ttyh1 protein activity. An RNAi molecule capable of regulating Ttyh1 gene expression, but is not limited thereto, may comprise one or more selected from an antisense oligonucleotide, siRNA, shRNA, miRNA, a ribozyme and PNA, which complementarily bind to mRNA of the Ttyh1 gene, and a material for inhibiting Ttyh1 protein activity may comprise natural substances and chemicals such as an aptamer, an antibody, a peptide, a peptidomimetic and a substrate analog, which specifically bind to Ttyh1, without limitation.

The composition of the present invention may comprise an antisense oligonucleotide comprising a sequence complementary to a base sequence represented by SEQ ID NO: 1, which is a part of the gene sequence encoding Ttyh1, siRNA, shRNA, or miRNA, a ribozyme or a PNA molecule, which targets the base sequence of SEQ ID NO: 1, as an active ingredient.

The term "antisense oligonucleotide" used herein refers to DNA or RNA containing a nucleic acid sequence complementary to a specific mRNA sequence, or a derivative thereof, and binding to the complementary sequence in mRNA, thereby inhibiting the translation of mRNA into a protein. The antisense sequence of the present invention refers to a DNA or RNA sequence which is complementary to Ttyh1 and capable of binding to Ttyh1 mRNA, and inhibits an essential activity for translation, translocation into the cytosol, maturation or all other biological functions of Ttyh1 mRNA. The length of an antisense nucleic acid may be 6 to 100 bases, preferably, 8 to 60 bases, and more preferably, 10 to 40 bases.

The term "siRNA" used herein refers to a nucleic acid molecule capable of mediating RNA interference or gene silencing. Since siRNA can inhibit the expression of a target gene, it is provided as an effective gene knock-down method or gene therapy method.

The siRNA molecule of the present invention may have a double-stranded structure in which a sense strand (sequence corresponding to Ttyh1 mRNA sequence) and an antisense strand (sequence complementary to Ttyh1 mRNA sequence) are located opposite to each other. In addition, the siRNA molecule of the present invention may have a single-stranded structure having self-complementary sense and antisense strands. As an exemplary example, the siRNA molecule may include a nucleotide sequence complementary to SEQ ID NO: 1 of the present invention.

The term "small hairpin RNA or short hairpin RNA (shRNA)" refers to an RNA sequence forming a rigid hairpin turn, and may be used to inhibit gene expression through RNA interference. Generally, shRNA mainly uses a U6 promoter capable of expressing shRNA using a vector for cell introduction. Such a vector is always transferred to a daughter cell to inherit gene silencing. The shRNA hairpin structure is degraded by siRNA, which is intracellular machinery, and binds to an RNA-induced silencing complex. The above-described complex binds to mRNA matched to the siRNA binding thereto and thus degraded. shRNA is transcribed by RNA polymerase III, and shRNA production in mammalian cells may lead to an interferon response if cells recognize shRNA as viral attack and find a defensive means.

In an exemplary embodiment of the present invention, as a RNAi molecule specifically binding to the Ttyh1 gene, most preferably, the shRNA (shTtyh1) was used, and may comprise a sequence complementary to SEQ ID NO: 1 of the present invention. When Ttyh1 expression was inhibited through the shTtyh1 action, it was confirmed that γ-secretase activity was actually decreased.

The term "microRNA (miRNA)" used herein refers to a single-stranded RNA molecule of 21 to 25 nucleotides, and a regulatory material that controls gene expression in eukaryotes through disruption of target mRNA or suppression thereof in translation. The miRNA is formed with a two-step process. The first miRNA transcriptome (primary miRNA) is formed as a 70 to 90-base stem-loop structure, that is, pre-miRNA, by Drosha, which is an RNase type enzyme, in the nucleus, translocated into the cytosol, and digested by dicer, which is an enzyme, resulting in mature miRNA of 21 to 25 bases. The miRNA produced thereby complementarily binds to target mRNA for transcription, and then serves as a post-transcriptional gene suppressor, thereby inducing translation inhibition and mRNA destabilization.

In addition, the composition of the present invention may comprise an aptamer, a Ttyh1 antibody, a peptide, a peptidomimetic or a substrate analog, which inhibits Ttyh1 protein activity, without limitation.

The term "aptamer" used herein is a nucleic acid molecule having a binding activity to a predetermined target molecule, and may be obtained by isolating an oligomer binding to a specific chemical molecule or biological molecule with high affinity and selectivity by an evolutionary method using an oligonucleotide library called systematic evolution of ligands by exponential enrichment (SELEX). The aptamer may bind to a predetermined target molecule, thereby inhibiting the activity of the predetermined target molecule. The aptamer of the present invention may be RNA, DNA, a modified nucleic acid or a mixture thereof, and is formed in a linear or cyclic form without limitation.

The term "antibody" used herein may be a monoclonal or polyclonal antibody which inhibits Ttyh1 protein activity. The antibody inhibiting the Ttyh1 protein activity may be specifically bound to the Ttyh1 protein and thus effectively inhibit the Ttyh1 protein activity. The antibody specifically binding to the Ttyh1 protein may be prepared by a method known to those of ordinary skill in the art, or a commercially available antibody may be used. In addition, the antibody inhibiting the Ttyh1 protein activity comprises a functional fragment of the antibody in addition to a full-length complete form having two heavy chains and two light chains so long as activity may be inhibited by specifically binding to the Ttyh1 protein. The functional fragment of the antibody refers to a fragment at least having an antigen-binding function, which comprises Fab, F(ab'), F(ab')2 or Fv.

In addition, all of a peptide, a peptidomimetic and a substrate analog, which can be comprised as a Ttyh1 protein activity inhibitor of the present invention, inhibit protein activity by inhibiting a specific domain of the Ttyh1 protein. The peptidomimetic may be a peptide or non-peptide, and may consist of amino acids linked through non-peptide bonds, such as psi (ψ) bonds. In addition, the peptidomimetic may be a "conformationally constrained" peptide, a cyclic mimetic, or a cyclic mimetic comprising at least one exocyclic domain, a linking part (linker amino acid) and an active part. The peptidomimetic may be a novel small molecule which is structurally similar to secondary structure characteristics of the Ttyh1 protein, mimic an inhibitory property of a macromolecule such as an antibody or a water-soluble receptor, and act with an effect equivalent to a natural antagonist.

Meanwhile, the composition of the present invention may down-regulate the action of γ-secretase that releases the intracellular domain of an amyloid precursor protein (APP), and thus inhibit a process of expressing amyloid β by translocating the intracellular domain of APP into the nucleus. In one exemplary embodiment of the present invention, the composition of the present invention was subjected to a luciferase assay through a C99-GVP (Gal4 DNA-binding/VP16 transfection) reporter by taking advantage of the release of the intracellular domain of a C99 protein, which is a part of APP, by γ-secretase and nuclear translocation thereof. As a result, in Ttyh1 gene expression in neural stem cells, it was confirmed that γ-secretase activity was greatly increased, and on the contrary, it was confirmed that, when Ttyh1 gene expression was inhibited, the γ-secretase activity was decreased.

The composition of the present invention may be a pharmaceutical composition. The pharmaceutical composition of the present invention includes a pharmaceutically acceptable carrier. The pharmaceutically acceptable carrier included in the pharmaceutical composition of the present invention is generally used in formulation, and includes lactose, dextrose, sucrose, sorbitol, mannitol, mannitol, starch, acacia gum, calcium phosphate, alginate, gelatin, calcium phosphate, microcrystalline cellulose, polyvinylphyrrolidone, cellulose, water, syrup, methyl cellulose, methylhydroxybenzoate, propyhydroxybenzoate, talc, magnesium stearate and mineral oil, but the present invention is not limited thereto. The pharmaceutical composition of the present invention may further include a lubricant, a wetting agent, a sweetening agent, a flavoring agent, an emulsifying agent, a suspending agent, a preservative, etc. in addition to the above-described components. Suitable pharmaceutically acceptable carriers and formulations are disclosed in detail in Remington's Pharmaceutical Sciences (19th ed., 1995).

A suitable dose of the pharmaceutical composition of the present invention may be variously prescribed according to parameters such as formulation methods, administration methods, a patient's age, body weight and sex, morbidity, diet, administration time, administration routes, absorption of an active ingredient in the body, inactivity, concomitant drugs, an excretion rate, and responsiveness. Preferably, the dose of the pharmaceutical composition of the present invention is 0.0001 ng/kg (body weight) to 100 mg/kg (body weight) per day.

The pharmaceutical composition of the present invention may be formulated with pharmaceutically acceptable carriers and/or excipients according to a method that can be easily performed by those of ordinary skill in the art to which the present invention belongs, and prepared in the form of a single-dose or multi-dose container. Here, the pharmaceutical composition of the present invention may be prepared in the form of a solution in an oil or aqueous medium, a suspension, an emulsion, an extract, a powder, granules, tablets or capsules, and may further include a dispersant or a stabilizer.

In addition, the composition of the present invention may be prepared in a health functional food for preventing Alzheimer's disease or improving a symptom. The health functional food means food manufactured and processed using a raw material or component having useful functions for the human body according to the Health Functional Food Act (No. 6722), and food which is ingested in order to regulate nutrients for the structure and functions of the human body or to obtain a hygienically advantageous effect such as physiological action. The health functional food composition of the present invention may be formulated in the form of a conventional health functional food known in the art, for example, granules, tablets, pills, a suspension, an emulsion, a syrup, gum, tea, jelly, various types of beverages, drinks, alcoholic beverages or the like, and there is no particular limitation to the type of the health functional food.

The health functional food composition of the present invention may be in an arbitrary herbal form suitable for being administered to an animal body as well as the human body, and more specifically, an arbitrary form conventionally used in oral administration, for example, a solid type such as food, feed, a food or feed additive and supplement, fortified food or feed, a tablet, a pill, a granule, a capsule or a foam mixture, or a liquid type such as a solution, a suspension, an emulsion, a beverage or a paste. The health functional food composition of the present invention may contain a nutrient, a vitamin, an electrolyte, a sweetening agent, a coloring agent, an organic acid or a preservative, and these components may be used independently or in combination thereof.

In addition, the present invention provides a method of preventing or treating Alzheimer's disease, which comprises administering a pharmaceutical composition comprising a Ttyh1 gene expression inhibitor or a Ttyh1 protein activity inhibitor as an active ingredient to a subject.

In addition, the present invention provides a method of screening a material for preventing or treating Alzheimer's disease, which comprises: treating Ttyh1 protein-expressing cells with a test material; measuring a Ttyh1 expression level in the Ttyh1 protein-expressing cells; and determining the test material as a material for treating Alzheimer's disease when the Ttyh1 expression level is decreased, compared with a control which is not treated with the test material.

In an exemplary embodiment of the present invention, the Ttyh1 expression level may be measured by any one selected from the group consisting of immunoprecipitation, radioimmunoassay (RIA), enzyme-linked immunosorbent assay (ELISA), immunohistochemistry, RT-PCR, Western blotting and flow cytometry (FACS).

In addition, the present invention provides a method of screening a material for preventing or treating Alzheimer's disease, which comprises: treating a Ttyh1 protein with a test material; measuring a degree of Ttyh1 activity; and determining the test material as a material for treating Alzheimer's disease when the degree of the Ttyh1 protein activity is decreased, compared with a control which is not treated with the test material.

In an exemplary embodiment of the present invention, the degree of the Ttyh1 activity may be measured by any one selected from the group consisting of SDS-PAGE, immunofluorescence, ELISA, mass spectrometry and a protein chip.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, the present invention will be described in further detail with reference to examples. The examples are merely provided to more fully describe the present invention, and it will be obvious to those of ordinary skill in the art that the scope of the present invention is not limited to the following examples.

Experimental Methods

1. Cell Culture 293T cells were grown in a Dulbecco Modified Eagle Medium (DMEM) supplemented with 10% Fetal Bovine Serum (FBS) and 50 µg/ml of antibiotics (penicillin and streptomycin). Neural stem cells (NSCs) were prepared by extracting the brain from an ICR mouse embryo at 14.5 days after gestation, and among these cells, sectioning NSCs in ganglionic projections and the cerebral cortex. The sectioned NSCs were incubated in DMEM/F12 (Invitrogen) supplemented with B27 (GIBCO), penicillin & streptomycin, and FGF2.

2. Virus Infection

To construct an expression vector of Ttyh1 gene, total RNA was isolated from mouse primary neural precursor cells using the TRIzol reagent (Invitrogen). To synthesize the isolated RNA (2 µg) and oligo primers (Promega) as single-stranded cDNA, the reaction was carried out with sequences of SEQ ID NO: 2 and SEQ ID NO: 3 as primers using a reverse transcription kit (Promega).

The amplified sequence was first replicated in a pGem-T Easy vector (Promega), and then introduced into a retroviral vector MSIG at a BamH1 site. The retroviral vector programmed to express the Ttyh1 gene was introduced into 293T cells by transfection, thereby obtaining virus particles. The virus particles were added to the neural stem cell culture for infection.

3. RNA Purification and cDNA Synthesis

The virus-infected neural stem cells were incubated for 2 days, and then RNA purification was performed using TRIzol (Takara) and chloroform (Sigma). Subsequently, cDNA synthesis was performed through a reverse transcription process. The expression of respective genes was confirmed from the synthesized cDNA as a template using primers associated with Hes1, Hes5, Hey1, β-actin and Ttyh1 (Hes1: SEQ ID NOs: 4 and 5, Hes5: SEQ ID NOs: 6 and 7, Hey1: SEQ ID NOs: 8 and 9, β-actin: SEQ ID NOs: 10 and 11, and Ttyh1: SEQ ID NOs: 12 and 13). As a machine for qRT-PCR, a product manufactured by Takara was used.

4. Western Blotting

The virus-infected NSCs were lysed with lysis buffer (RIPA) at 4° C. for 30 minutes. Afterward, following addition of a 2× loading dye, the resultant was boiled at 100° C. for 10 minutes, thereby obtaining a sample. After electrophoresis of the sample, the protein of interest was transferred to a membrane, and reacted with antibodies, and subjected to western blotting. The antibodies used herein were β-actin, Cleaved Notch1 (Val1744), Rer1, and myc. HA.

5. Luciferase Reporter Assay

NSCs were transfected with control vectors having Ttyh1, dEN-GVP, UAS-luc and *Renilla*, and the experiment was performed using a luciferase assay kit (Promega).

Experimental Results

1. Gamma (γ)-Secretase Activity-Promoting Effect of Ttyh1

Figure 1:
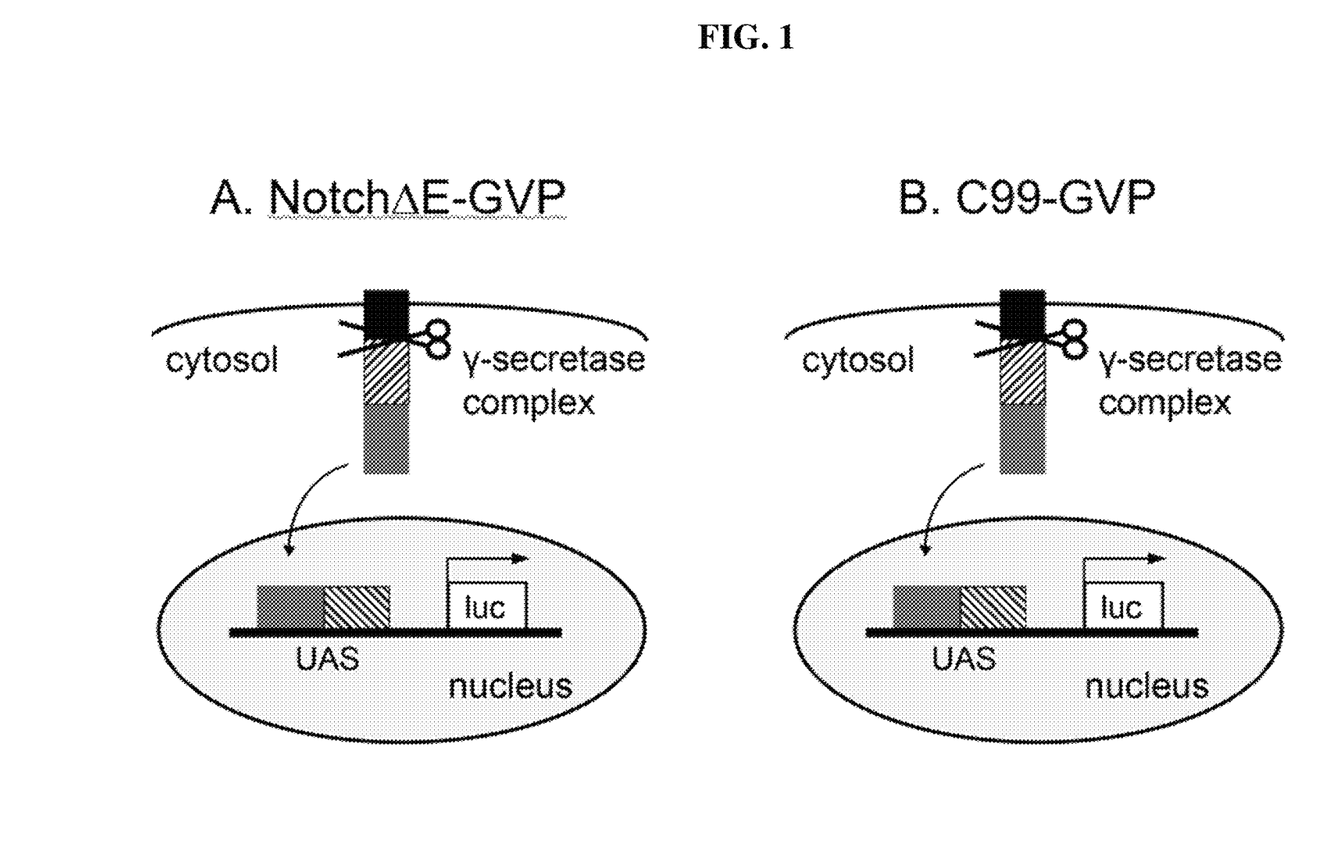
FIG. 1 is a schematic diagram of the action of γ-secretase involved in a Notch pathway and APP: A illustrates that NICD is released by γ-secretase, is translocated into the nucleus, and increases the activity of a UAS promoter in the nucleus, which can be confirmed through a luciferase assay; and B illustrates that a C99 protein intracellular domain, which is a part of APP, is released, is translocated into the nucleus, and increases the activity of the UAS promoter through a mechanism similar to A, and therefore, amyloid β production can also be assessed by measuring luciferase activity.
Figure 2:
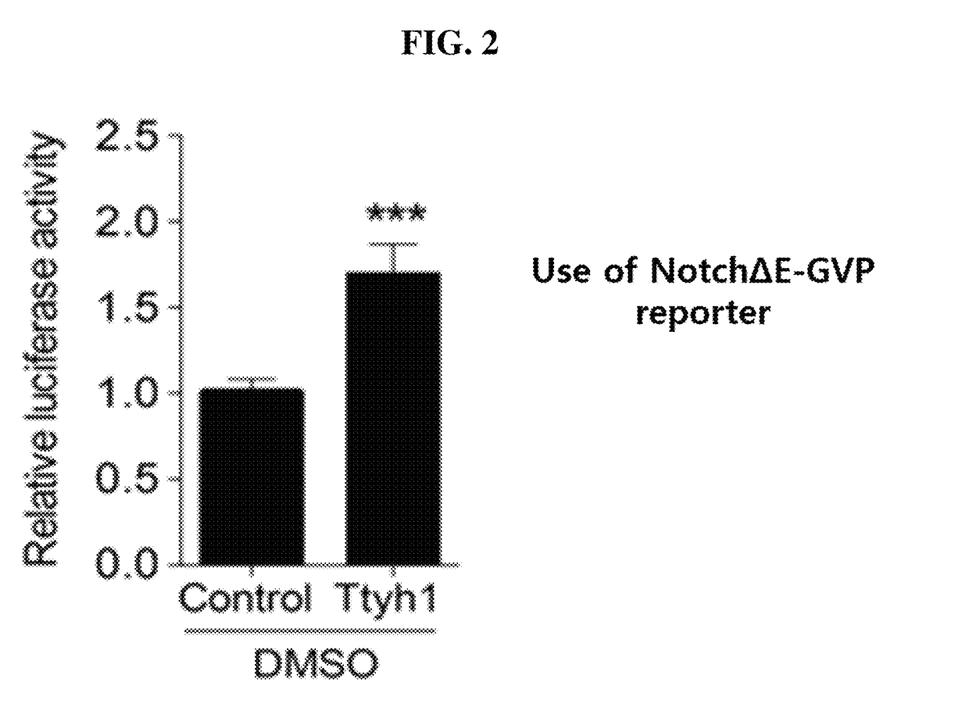
FIGS. 2 and 3 show results of confirming the action of Ttyh1 for regulating γ-secretase activity involved in a Notch pathway, confirming that, when Ttyh1 is expressed, γ-secretase activity increases, and when the Ttyh1 expression is inhibited, γ-secretase activity decreases.
Figure 3:
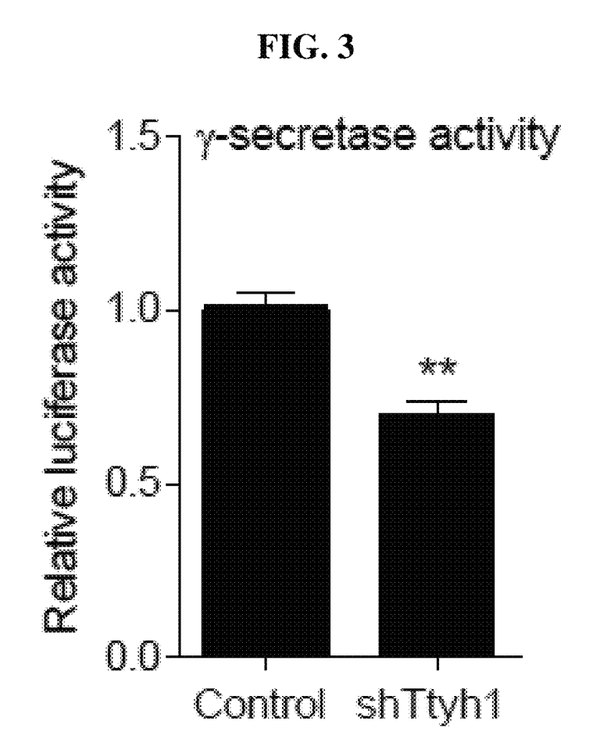

When NICD is cleaved by γ-secretase, a domain of the Notch protein in the cytosol is translocated into the nucleus. Then, as UAS promoter activity increased, luciferase expression increased, and this luciferase activity was measured to confirm the γ-secretase-mediated activation of Notch signaling. As a result, the higher the γ-secretase activity, the higher the luciferase protein expression, which was observed in a luciferase assay. FIG. 1A is a schematic diagram illustrating that the Notch protein is cleaved by γ-secretase, bound with the UAS promoter to be involved in its expression, and FIGS. 2 and 3 show the results obtained through luciferase activity, showing that the γ-secretase activity is actually regulated by Ttyh1 expression.

Figure 4:
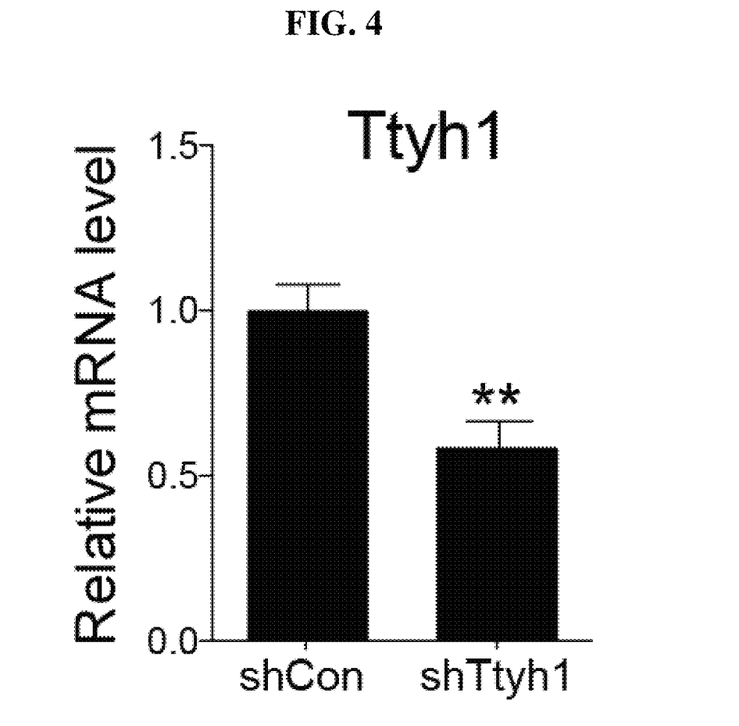
FIG. 4 shows the result of confirming the actual reduction of mRNA of Ttyh1 when shTtyh1 is expressed.
Figure 5:
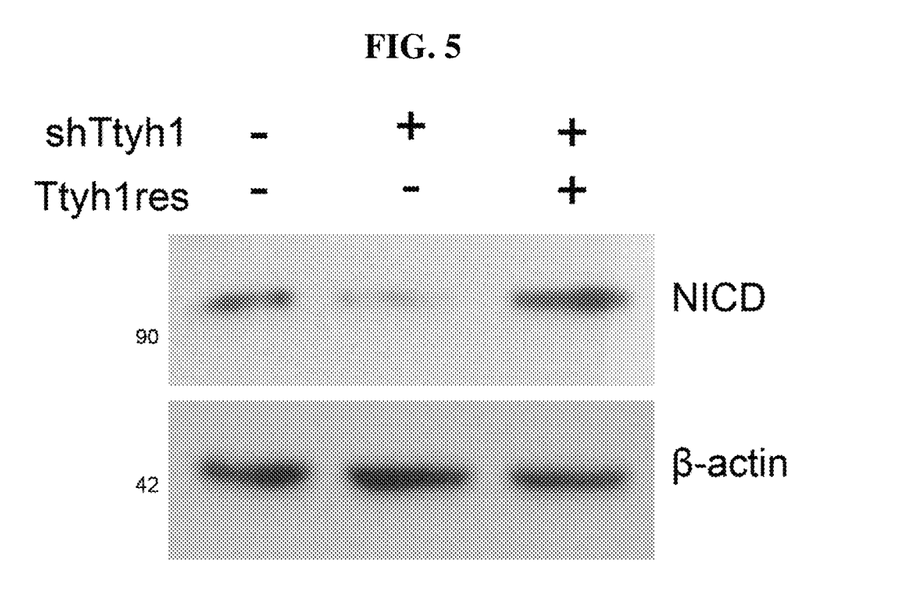
FIG. 5 shows whether γ-secretase activity is associated with a change in NICD production according to a change in expression level of Ttyh1. Western blotting confirmed that, upon shTtyh1 expression, an NICD expression level was decreased, and when Ttyh1 having a resistance to shTtyh1 is expressed, NICD production is increased again.

In addition, when a C99 intracellular domain, which is a part of an amyloid precursor protein (APP), is cleaved by γ-secretase, the domain of APP in the cytosol is translocated into the nucleus, resulting in an increase in UAS promoter activity and thus an increase in luciferase expression. Likewise, as a result of measuring amyloid β production activity, which is mediated by γ-secretase, through this luciferase activity, as shown in FIGS. 4 and 5, it was confirmed that when the C99 intracellular domain, which is a part of the APP protein, was cleaved by γ-secretase, the domain of APP in the cytosol was translocated into the nucleus, resulting in the increase in UAS promoter activity, and thus the luciferase expression was regulated, as assessed by Ttyh1 expression.

In other words, from the above-described experimental results, it was demonstrated that the amyloid precursor protein C99 can be activated by the action of γ-secretase, and the γ-secretase activity increases as the Ttyh1 expression increases. It was concluded that Ttyh1 plays a critical role in synthesis of amyloid β by activating an amyloid precursor protein.

2. Confirmation of Change in NICD Production by Regulating Ttyh1 Expression

To confirm a Ttyh1 expression regulatory effect, Ttyh1 expression was inhibited using shRNA (shTtyh1). After being first replicated in a pGem-T Easy vector (Promega), shTtyh1 was introduced into a retroviral vector MSIG at a BamH1 site, and the vector was injected into neural stem cells. As a result, as shown in FIG. 4, it can be confirmed that when shTtyh1 was expressed, a Ttyh1 mRNA level was greatly reduced.

To check if the change in γ-secretase activity caused by the change in Ttyh1 expression leads to an actual change in NICD production, a NICD protein level in neural stem cells was determined by western blotting. As a result, as shown in FIG. 5, when Ttyh1 expression was reduced using shRNA (shTtyh1), it was observed that the NICD protein level was greatly decreased, and when an shRNA-resistant Ttyh1 gene was expressed again, it was confirmed that the NICD level was increased, demonstrating that Ttyh1 inhibition induces the inhibition of γ-secretase activity, and thus the NICD production was reduced.

Figure 6:
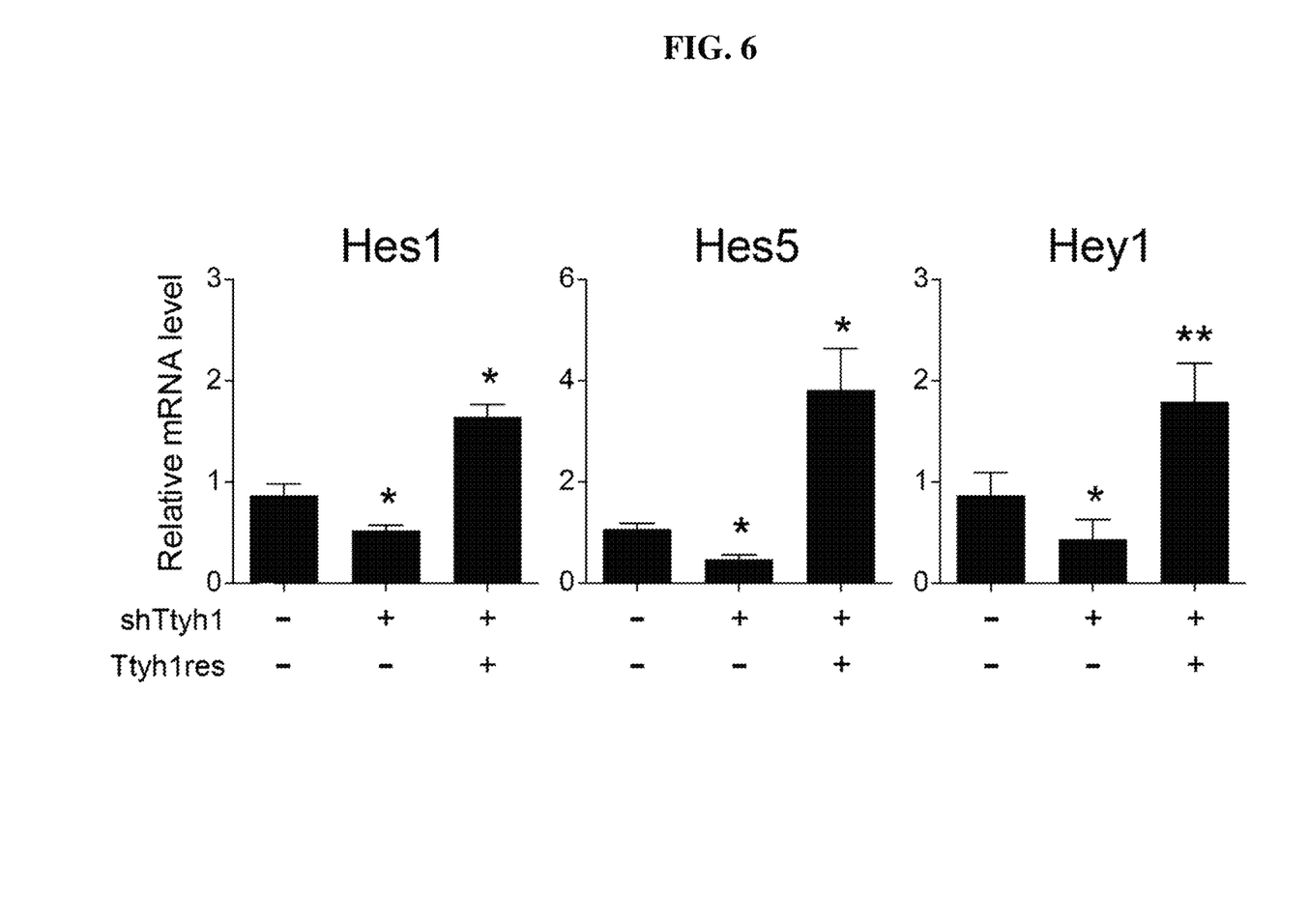
FIG. 6 shows the result of confirming mRNA expression levels of Hes1, Hes5 and Hey1, which are target genes of a Notch pathway, according to Ttyh1 expression, and when Ttyh1 expression is inhibited by expressing shTtyh1, the mRNA expression level of a target gene is decreased, and when Ttyh1 expression is increased, the mRNA expression level of a target gene is increased again. This demonstrates that Ttyh1 inhibition inhibits γ-secretase activity, and decreases NICD production, resulting in inhibiting the target gene expression of Notch.

In addition, neural stem cells were infected with a Ttyh1-associated gene, and after two days, treated with TRIzol to extract mRNA and synthesize cDNA. Through qRT-PCR, mRNA variations of representative target genes, Hes1, Hes5 and Hey1, of a Notch signaling pathway were assessed, confirming that, as shown in FIG. 6, when Ttyh1 expression was reduced using shRNA (shTtyh1), the levels of these Notch target genes were reduced, and when the shRNA-resistant Ttyh1 gene was expressed again, the target gene levels were increased. This demonstrates that Ttyh1 inhibition induces the inhibition of γ-secretase activity, resulting in decreased NICD production and eventually the inhibition of the expression of the target genes of Notch.

Figure 7:
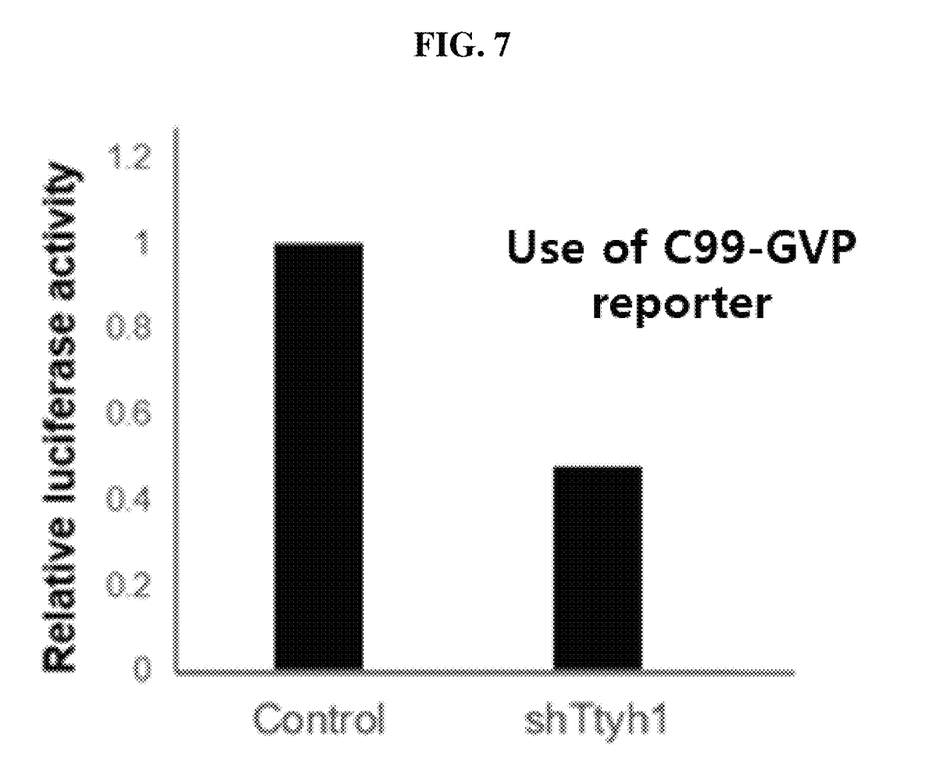
FIGS. 7 and 8 show the results of confirming whether amyloid β is produced according to the regulation of the expression of Ttyh1 gene, confirming that, when Ttyh1 is expressed, γ-secretase activity increases, and when Ttyh1 expression is inhibited using shTtyh1, the reduction in γ-secretase activity is confirmed by the expression level of a C99-GVP reporter in which GVP inducing transcription activation is bound to C99, which is the intracellular domain of APP.
Figure 8:
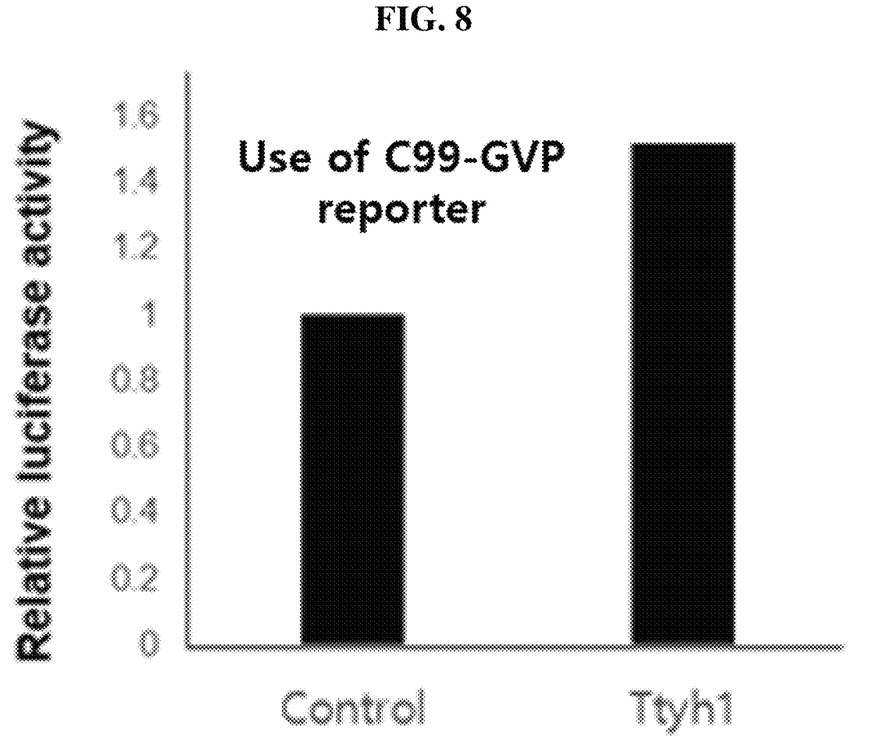

3. Confirmation of APP Cleavage Efficiency of γ-Secretase by Regulation of Ttyh1 Expression It was confirmed whether the change in γ-secretase activity by the change in Ttyh1 expression can affect amyloid β production. When the intracellular domain of APP was cleaved by γ-secretase, amyloid β was produced, and to quantitatively measure this reaction, a C99-GVP reporter in which APP intracellular domain C99 and transcription activation domain GVP are fused was used. There is an APP motif cleaved by γ-secretase activity between the C99 and GVP domains. The APP motif is the same as that used when amyloid β in APP is cleaved by γ-secretase. GVP isolated from C99 due to the γ-secretase activity was translocated into the nucleus to increase the expression of a luciferase gene. That is, the amount of amyloid β produced by the γ-secretase activity was measured through luciferase activity. As a result, as shown in FIGS. 7 and 8, when the Ttyh1 expression level was reduced by shTtyh1, it was confirmed that the APP cleavage efficiency by γ-secretase was greatly reduced, and on the contrary, when the Ttyh1 expression level was increased, the APP cleavage efficiency by γ-secretase greatly increased. Therefore, it can be quantitatively confirmed that the amyloid production may be regulated through the regulation of Ttyh1 expression.

The present invention provides a use of an RNAi molecule specifically linked with Ttyh1 gene, which is capable of regulating the expression of the Ttyh1 gene, as a composition for preventing or treating Alzheimer's disease. The composition of the present invention is directly involved in the mechanism of producing amyloid β, which becomes the cause of Alzheimer's disease, and by inhibiting the expression of Ttyh1, which is the gene involved in the mechanism described above, a fundamental therapeutic method for the cause of Alzheimer's disease can be suggested.

The present invention has been described with reference to the exemplary embodiments described above. The exemplary embodiments disclosed herein can be easily modified into other specific forms without changing the technical spirit or essential features of the present invention. Therefore, the disclosed embodiments are to be considered in an illustrative, rather than a restrictive sense. The scope of the present invention is defined by the claims, rather than the above-described description, and all differences within the scope of equivalents thereof should be construed as being included in the present invention.

What is claimed is:

1. A method of treating Alzheimer's disease in a subject in need thereof, comprising:

administering a pharmaceutical composition comprising a Ttyh1 gene expression inhibitor as an active ingredient to the subject, wherein Ttyh1 gene expression inhibitor is shRNA or siRNA comprising a sequence that is complementary to Ttyh1.

2. The method according to claim 1, wherein a target of the Ttyh1 gene expression inhibitor comprises a base sequence of SEQ ID NO: 1.

3. The method according to claim 1, wherein the Ttyh1 gene expression inhibitor is shRNA as a RNAi molecule capable of regulating Ttyh1 gene expression.

4. The method according to claim 1, wherein the Ttyh1 gene expression inhibitor down-regulates γ-secretase activity to inhibit the release of the intracellular domain of an amyloid precursor protein (APP).

* * * * *

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Ttyh1

<400> SEQUENCE: 1
agacactgaa tgtgacagaa                                              20

<210> SEQ ID NO 2
<211> LENGTH: 32
<212> TYPE: DNA
<213> ORGANISM: Artificial Sequence
<220> FEATURE:
<223> OTHER INFORMATION: Ttyh1-F

<400> SEQUENCE: 2
aacgcgtgcc accatggggg caccccggg ct                                 32

<210> SEQ ID NO 3
<211> LENGTH: 52
<212> TYPE: DNA
<213> ORGANISM: Artificial Sequence
<220> FEATURE:
<223> OTHER INFORMATION: Ttyh1-R

<400> SEQUENCE: 3
tggatcctca caagtcctct tcagaaatga gcttgatgga agactgccac tg           52

<210> SEQ ID NO 4
<211> LENGTH: 20
<212> TYPE: DNA
<213> ORGANISM: Artificial Sequence
<220> FEATURE:
<223> OTHER INFORMATION: Hes1 F

<400> SEQUENCE: 4
taccccagcc agtgtcaaca                                              20

<210> SEQ ID NO 5
<211> LENGTH: 19
<212> TYPE: DNA
<213> ORGANISM: Artificial Sequence
<220> FEATURE:
<223> OTHER INFORMATION: Hes1 R

<400> SEQUENCE: 5
tcttgccctt cgcctcttc                                               19

<210> SEQ ID NO 6
<211> LENGTH: 20
<212> TYPE: DNA
<213> ORGANISM: Artificial Sequence
<220> FEATURE:
<223> OTHER INFORMATION: Hes5 F

<400> SEQUENCE: 6
caaggagaaa aaccgactgc                                              20

<210> SEQ ID NO 7
<211> LENGTH: 20
<212> TYPE: DNA
<213> ORGANISM: Artificial Sequence

```
<220> FEATURE:
<223> OTHER INFORMATION: Hes5 R

<400> SEQUENCE: 7
gctggaagtg gtaaagcagc                                              20

<210> SEQ ID NO 8
<211> LENGTH: 20
<212> TYPE: DNA
<213> ORGANISM: Artificial Sequence
<220> FEATURE:
<223> OTHER INFORMATION: Hey1 F

<400> SEQUENCE: 8
tgagctgaga aggctggtac                                              20

<210> SEQ ID NO 9
<211> LENGTH: 20
<212> TYPE: DNA
<213> ORGANISM: Artificial Sequence
<220> FEATURE:
<223> OTHER INFORMATION: Hey1 R

<400> SEQUENCE: 9
accccaaact ccgatagtcc                                              20

<210> SEQ ID NO 10
<211> LENGTH: 24
<212> TYPE: DNA
<213> ORGANISM: Artificial Sequence
<220> FEATURE:
<223> OTHER INFORMATION: beta-actin F

<400> SEQUENCE: 10
caaaagccac ccccactcct aaga                                         24

<210> SEQ ID NO 11
<211> LENGTH: 22
<212> TYPE: DNA
<213> ORGANISM: Artificial Sequence
<220> FEATURE:
<223> OTHER INFORMATION: beta-actin R

<400> SEQUENCE: 11
gccctggctg cctcaacacc tc                                           22

<210> SEQ ID NO 12
<211> LENGTH: 21
<212> TYPE: DNA
<213> ORGANISM: Artificial Sequence
<220> FEATURE:
<223> OTHER INFORMATION: hTTYH1_F

<400> SEQUENCE: 12
gtggctggtg atcgtgatga c                                            21

<210> SEQ ID NO 13
<211> LENGTH: 23
<212> TYPE: DNA
<213> ORGANISM: Artificial Sequence
<220> FEATURE:
<223> OTHER INFORMATION: hTTYH1_R

<400> SEQUENCE: 13
tgcagaggag ataatagctc agg                                          23
```